(12) United States Patent
Bunick et al.

(10) Patent No.: US 7,914,811 B2
(45) Date of Patent: Mar. 29, 2011

(54) BRITTLE-COATING, SOFT CORE DOSAGE FORM

(75) Inventors: Frank J. Bunick, Randolph, NJ (US); John J. Burke, Bensalem, PA (US); Timothy P. Gilmor, Orefield, PA (US); Michelle Papalini, Bensalem, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 321 days.

(21) Appl. No.: 09/896,052

(22) Filed: Jun. 29, 2001

(65) Prior Publication Data

US 2003/0017202 A1    Jan. 23, 2003

(51) Int. Cl.
*A61K 9/28*     (2006.01)
*A61K 9/24*     (2006.01)
*A61K 9/20*     (2006.01)

(52) U.S. Cl. ......... 424/441; 424/464; 424/472; 424/474

(58) Field of Classification Search .................. 424/489, 424/400, 490, 474, 472, 439, 440, 441, 464, 424/465
See application file for complete search history.

(56) References Cited

U.S. PATENT DOCUMENTS

| | | | |
|---|---|---|---|
| 4,260,596 A * | 4/1981 | Mackles | 424/440 |
| 4,271,142 A * | 6/1981 | Puglia et al. | 424/440 |
| 4,327,076 A | 4/1982 | Puglia et al. | |
| 4,684,534 A | 8/1987 | Valentine | |
| 4,725,441 A | 2/1988 | Porter et al. | |
| 4,753,790 A * | 6/1988 | Silva et al. | 427/2.18 |
| 4,800,087 A * | 1/1989 | Mehta | 424/497 |
| 4,828,845 A | 5/1989 | Zamudio-Tena et al. | |
| 4,851,226 A | 7/1989 | Julian et al. | |
| 5,075,114 A | 12/1991 | Roche | |
| 5,102,664 A | 4/1992 | Day | |
| 5,362,508 A | 11/1994 | Wheeler et al. | |
| 5,489,436 A | 2/1996 | Hoy et al. | |
| 5,578,316 A * | 11/1996 | Bhardwaj et al. | 424/441 |
| 5,618,527 A | 4/1997 | Mendes et al. | |
| 6,017,567 A | 1/2000 | Rosenplenter | |
| 6,060,078 A * | 5/2000 | Lee | 424/440 |
| 6,077,557 A | 6/2000 | Gordon et al. | |
| 6,139,865 A * | 10/2000 | Friend et al. | 424/441 |
| 6,432,441 B1 * | 8/2002 | Bealin-Kelly et al. | 424/440 |
| 6,432,442 B1 * | 8/2002 | Buehler et al. | 424/441 |

FOREIGN PATENT DOCUMENTS

| | | |
|---|---|---|
| EP | 0950402 A2 * | 10/1999 |
| WO | WO 93/13758 A1 | 7/1993 |

OTHER PUBLICATIONS

Bauer K. H. et al., Pharmazeutische Technologie. Georg Thieme Verlag Stuttgart 1991, pp. 314-315.
*Pharmaceutical Dosage Forms*; Edited by Liebermari H.A., Lachman, L., and Schwartz, J.B.; Marcel Dekker, Inc., New York, vol. 1, pp. 285-328, 1989.
*Pharmaceutical Dosage Forms*; Edited by Lieberman, H.A., Lachman, L., and Schwartz J.B.; Marcel Dekker, Inc., New York, vol. 2, pp. 213-217 and 327-329, 1990.
*Pharmaceutical Dosage Forms*; Edited by Lieberman, H.A., Lachman, L., Schwartz, J.B.; Marcel Dekker, Inc., New York, vol. 3, pp. 199-302, 1990.
*The Theory and Practice of Industrial Pharmacy*; Lachman, L., Lieberman, H.A., Kanig, J.L.; Lea & Febiger, 3rd ed., 1986; pp. 293-345.
*Sugar Confectionery Manufacture*; Edited by Jackson, E.B.; Van Nostrand Reinhold, New York, 1990, pp. 205-206.

\* cited by examiner

*Primary Examiner* — S. Tran

(57) ABSTRACT

The present invention provides an oral dosage form for delivering active agents having a soft core with an active agent particles, which have an average size of greater than about 50 μm, and a brittle shell encasing the soft core, wherein the weight ratio of drug particles to shell being from about 1.0:0.5 to about 1.0:15.

14 Claims, No Drawings

BRITTLE-COATING, SOFT CORE DOSAGE FORM

FIELD OF THE INVENTION

The present invention is directed to an oral dosage form for administering an active agent having a soft core encased in a brittle coating.

BACKGROUND OF THE INVENTION

Active agents, e.g., pharmaceuticals, nutraceuticals, and the like, intended for oral administration are often provided in solid form as tablets, capsules, pills, lozenges, or granules. Oral dosage forms are swallowed whole, chewed in the mouth, or dissolved sublingually. Chewable dosage forms are often employed in the administration of active agents where it is impractical to provide a tablet for swallowing whole, where it is desirable to make an active agent available topically in the mouth or throat for both local effects or systemic absorption and to improve drug administration in pediatric and geriatric patients. With chewable dosage forms, the act of chewing disperses the particles of the dosage form and may increase the rate of absorption of any active agent present therein.

It has been observed that particles in chewable dosage forms leave a gritty sensation in the mouth that can be unpleasant, i.e., unpleasant mouthfeel. The term mouthfeel relates to the type of sensation or touch that a dosage form produces in the mouth upon ingestion and is not concerned with the chemical stimulation of olfactory nerves or taste buds. However, for a dosage form to be successful, the overall effect in the mouth is important. In general, a gritty texture is undesirable. A smooth texture is preferred. See, *Pharmaceutical Dosage Forms*, Edited by Leiberman, H. A. and Lachman, L. Marcel Dekker, Inc. New York, Volume 1, pp. 291.

In attempts to address some of the above issues, different formulations have been investigated. Formulations of nano- or macrogranulars have been reported in U.S. Pat. No. 5,618,527. In order to prevent the sensation of grittiness, U.S. Pat. No. 5,618,527 describes formulations in either liquid or tablet form consisting of spherical particles of not greater then 125 µm in diameter. Additionally, the particles are required to have smooth edges. These requirements severely limit the flexibility of delivery of the drug.

Another method of is described in U.S. Pat. No. 6,077,557. This patent describes incorporating a calcium component into a gel. In particular, the grittiness of the calcium component was avoided by utilizing a calcium source having a small particle size, 90% of the calcium particles being less than 150 µm and the best results were described as being obtained with a mean particle size of less than 50 µm.

An alternative attempt to reduce the sensation of grittiness by using a blend of a gritty drug product with a seedy fruit, such as strawberries, was described in U.S. Pat. No. 5,102,664. In this combination, the seedy fibrous fruit texture masks the grittiness of the active agent.

It is known to apply outer coatings to a chewable tablet in order to protect the soft core. Often such outer coatings contain cellulose derivatives as major ingredients, which have relatively high melting points, i.e., greater than 135° C. For example, PCT Application No. WO 93/13758 discloses the application of a thin layer of coating material such as a disaccharide, polysaccharide, or cellulose derivative onto a compressed tablet. U.S. Pat. No. 4,828,845 relates to the coating of a comestible with a coating solution comprising xylitol, a film-forming agent such as methyl cellulose, a binder, optionally a filler, and optionally a plasticizer such as polyethylene glycol, the balance of the solution being water. The plasticizer makes up only about 3 to 7 weight percent of the coating solution disclosed in the '845 patent. U.S. Pat. No. 4,327,076 discloses a compressed, soft, chewable tablet containing an antacid or other active agent that may be coated with a sealant or a spray coat of chocolate.

U.S. Pat. No. 6,017,567 discloses a sugar-free hard coating of edible, chewable, or pharmaceutical compositions. In particular, the hard coating was disclosed as being formed by treating a core with a sorbitol syrup and at least one other polyol in crystalline form. In particular, the hard coating of disclosed was believed to be useful for coating chewing gum, confectionery products (such as candies), chocolate and nuts.

Alternatively, as disclosed in U.S. Pat. No. 4,684,534, moisture-free soft tablets have been produced by compressing a combination of an active agent with a carbohydrate and a binder such that the open pore structure of the combination is destroyed only at the tablet surface. Because of their relatively brittle exterior, these tablets are resistant to moisture absorption; however, these tablets quickly liquefy and melt when chewed due to their open pore interior structure.

Yet another method for preparing soft cores in food products is disclosed in U.S. Pat. No. 5,362,508, wherein a core composition comprising a mixture of sucrose, invertase, and a fat component is coated with a second fat component. Upon incubation, short chain fatty acid residues from the second fat component migrated into the core fat component to yield a soft fat mixture in the core having a lower fat solids content.

A dosage form has now been discovered that masks the grittiness of the active agents contained therein. This dosage form not only effectively masks the taste and texture of the active agent, but it conveniently may be consumed anywhere without the need for water. The dosage form includes a soft core encased in a brittle coating. Surprisingly, the brittle coating of the present invention not only stabilizes the soft core, but it also provides a masking agent for the gritty texture of the active agent upon chewing

SUMMARY OF THE INVENTION

The present invention provides an oral dosage form for delivering active agents having a soft core with an active agent particles, which have an average size of greater than about 50 µm, and a brittle shell encasing the soft core, wherein the weight ratio of drug particles to shell being from about 1.0:0.5 to about 1.0:15.

DETAILED DESCRIPTION OF THE INVENTION

The term, "active agent" is used herein in a broad sense and encompasses any material that can be carried by or entrained in the system. For example, the active agent can be a pharmaceutical, nutraceutical, vitamin, dietary supplement, nutrient, or the like and combinations thereof.

The active agents useful herein can be selected from classes from those in the following therapeutic categories: ace-inhibitors; alkaloids; antacids; analgesics; anabolic agents; anti-anginal drugs; anti-allergy agents; anti-arrhythmia agents; antiasthmatics; antibiotics; anticholesterolemics; anticonvulsants; anticoagulants; antidepressants; antidiarrheal preparations; anti-emetics; antihistamines; antihypertensives; anti-infectives; anti-inflammatories; antilipid agents; antimanics; anti-migraine agents; antinauseants; antipsychotics; antistroke agents; antithyroid preparations; anabolic drugs; antiobesity agents; antiparasitics; antipsychotics; antipyretics; antispasmodics; antithrombotics; antitumor agents; antitussives; antiulcer agents; anti-uricemic agents; anxiolytic agents; appetite stimulants; appetite suppressants; beta-blocking agents; bronchodilators; cardiovascular agents; cerebral dilators; chelating agents; cholecystekinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypoglycemic agents; ion-exchange resins; laxatives; migraine treatments; mineral supplements; mucolytics, narcotics; neuroleptics; neuromuscular drugs; non-steroidal anti-inflammatories (NSAIDs); nutritional additives; peripheral vasodilators; polypeptides; prostaglandins; psychotropics; renin inhibitors; respiratory stimulants; sedatives; steroids; stimulants; sympatholytics; thyroid preparations; tranquilizers; uterine relaxants; vaginal preparations; vasoconstrictors; vasodilators; vertigo agents; vitamins; wound healing agents; and others.

Active agents that may be used in the invention include, but are not limited to: acetaminophen; acetic acid; acetylsalicylic acid, including its buffered forms; acrivastine; albuterol and its sulfate; alcohol; alkaline phosphatase; allantoin; aloe; aluminum acetate, carbonate, chlorohydrate and hydroxide; alprozolam; amino acids; aminobenzoic acid; amoxicillin; ampicillin; amsacrine; amsalog; anethole; ascorbic acid; aspartame; astemizole; atenolol; azatidine and its maleate; bacitracin; balsam peru; BCNU (carmustine); beclomethasone diproprionate; benzocaine; benzoic acid; benzophenones; benzoyl peroxide; benzquinamide and its hydrochloride; bethanechol; biotin; bisacodyl; bismuth subsalicylate; bornyl acetate; brompheniramine and its maleate; buspirone; caffeine; calamine; calcium carbonate, casinate and hydroxide; camphor; captopril; cascara sagrada; castor oil; cefaclor; cefadroxil; cephalexin; centrizine and its hydrochloride; cetirizine; cetyl alcohol; cetylpyridinium chloride; chelated minerals; chloramphenicol; chlorcyclizine hydrochloride; chlorhexidine gluconate; chloroxylenol; chloropentostatin; chlorpheniramine and its maleates and tannates; chlorpromazine; cholestyramine resin; choline bitartrate; chondrogenic stimulating protein; cimetidine; cinnamedrine hydrochloride; citalopram; citric acid; clarithromycin; clemastine and its fumarate; clonidine; clorfibrate; cocoa butter; cod liver oil; codeine and its fumarate and phosphate; cortisone acetate; ciprofloxacin HCl; cyanocobalamin; cyclizine hydrochloride; cyproheptadine; danthron; dexbrompheniramine maleate; dextromethorphan and its hydrohalides; diazepam; dibucaine; dichloralphenazone; diclofen and its alkali metal sales; diclofenac sodium; digoxin; dihydroergotamine and its hydrogenates/mesylates; diltiazem; dimethicone; dioxybenzone; diphenhydramine and its citrate; diphenhydramine and its hydrochloride; divalproex and its alkali metal salts; docusate calcium, potassium, and sodium; doxycycline hydrate; doxylamine succinate; dronabinol; efaroxan; enalapril; enoxacin; ergotamine and its tartrate; erythromycin; estropipate; ethinyl estradiol; ephedrine; epinephrine bitartrate; erythropoietin; eucalyptol; famotidine; fenoprofen and its metal salts; ferrous fumarate, gluconate and sulfate; fexofenadine; fluoxetine; folic acid; fosphenytoin; 5-fluorouracil (5-FU); fluoxetine; flurbiprofen; furosemide; gabapentan; gentamicin; gemfibrozil; glipizide; glycerine; glyceryl stearate; granisetron; griseofulvin; growth hormone; guafenesin; hexylresorcinol; hydrochlorothiazide; hydrocodone and its tartrates; hydrocortisone and its acetate; 8-hydroxyquinoline sulfate; hydroxyzine and its pamoate and hydrochloride salts; ibuprofen; indomethacin; inositol; insulin; iodine; ipecac; iron; isosorbide and its mono- and dinitrates; isoxicam; ketamine; kaolin; ketoprofen; lactic acid; lanolin; lecithin; leuprolide acetate; lidocaine and its hydrochloride salt; lifinopril; liotrix; loperamide, loratadine; lovastatin; luteinizing hormore; LHRH (lutenizing hormone replacement hormone); magnesium carbonate, hydroxide, salicylate, and trisilicate; meclizine; mefenamic acid; meclofenamic acid; meclofenamate sodium; medroxyprogesterone acetate; methenamine mandelate; menthol; meperidine hydrochloride; metaproterenol sulfate; methscopolamine and its nitrates; methsergide and its maleate; methyl nicotinate; methyl salicylate; methyl cellulose; methsuximide; metoclopramide and its halides/hydrates; metronidazole; metoprotol tartrate; miconazole nitrate; mineral oil; minoxidil; morphine; naproxen and its alkali metal sodium salts; nifedipine; neomycin sulfate; niacin; niacinamide; nicotine; nicotinamide; nimesulide; nitroglycerine; nonoxynol-9; norethindrone and its acetate; nystatin; octoxynol; octoxynol-9; octyl dimethyl PABA; octyl methoxycinnamate; omega-3 polyunsaturated fatty acids; omeprazole; ondansetron and its hydrochloride; oxolinic acid; oxybenzone; oxtriphylline; para-aminobenzoic acid (PABA); padimate-O; paramethadione; pentastatin; peppermint oil; pentaerythritol tetranitrate; pentobarbital sodium; perphenazine; phenelzine sulfate; phenindamine and its tartrate; pheniramine maleate; phenobarbital; phenol; phenolphthalein; phenylephrine and its tannates and hydrochlorides; phenylpropanolamine; phenytoin; pirmenol; piroxicam and its salts; polymicin B sulfate; potassium chloride and nitrate; prazepam; procainamide hydrochloride; procaterol; promethazine and its hydrochloride; propoxyphene and its hydrochloride and napsylate; pramiracetin; pramoxine and its hydrochloride salt; prochlorperazine and its maleate; propanolol and its hydrochloride; promethazine and its hydrochloride; propanolol; pseudoephedrine and its sulfates and hydrochlorides; pyridoxine; pyrolamine and its hydrochlorides and tannates; quinapril; quinidine gluconate and sulfate; quinestrol; ralitoline; ranitadine; resorcinol; riboflavin; salicylic acid; scopolamine; sesame oil; shark liver oil; simethicone; sodium bicarbonate, citrate, and fluoride; sodium monofluorophosphate; sucralfate; sulfanethoxazole; sulfasalazine; sulfur; sumatriptan and its succinate; tacrine and its hydrochloride; theophylline; terfenadine; thiethylperazine and its maleate; timolol and its maleate; thioperidone; tramadol; trimetrexate; triazolam; tretinoin; tetracycline hydrochloride; tolmetin; tolnaftate; triclosan; trimethobenzamide and its hydrochloride; tripelennamine and its hydrochloride; tripolidine hydrochloride; undecylenic acid; vancomycin; verapamil HCl; vidaribine phosphate; vitamins A, B, C, D, $B_1$, $B_2$, $B_6$, $B_{12}$, E, and K; witch hazel; xylometazoline hydrochloride; zinc; zinc sulfate; zinc undecylenate. Active agents may further include, but are not limited to food acids; insoluble metal and mineral hydroxides, carbonates, oxides, polycarbophils, and salts thereof, adsorbates of active drugs on a magnesium trisilicate base and on a magnesium aluminum silicate base, and mixtures thereof. Mixtures and pharmaceutically acceptable salts of these and other actives can be used.

The active agent can be in the form of a fine powder, granule, or large crystal, and has an average particle size from about 20 to about 1000 μm, also from about 150 μm to about 500 μm. Typically, the active agent used in the present invention has an average size of greater than 50 μm If the active agent has an objectionable taste, it may be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked active agents may also be employed. For example, acetaminophen particles that are encapsulated with ethylcellulose or other polymers by a coaccervation process may be used in the present invention. Coaccervation-encapsulated acetaminophen may be purchased commercially from Eurand America, Inc. Vandalia, Ohio, or from Circa Inc., Dayton, Ohio.

As used herein, all ranges provided are intended to expressly include at least all numbers that fall between the endpoints of ranges.

The present invention is directed to an oral dosage form for administering an active agent having a soft core encased in a brittle coating. In one method for making the oral dosage form of the present invention, the soft core is made first. After forming the soft core, the brittle coating may be added using conventional hard and soft panning techniques known to those in the art.

Soft cores of the present invention may be formed by direct compression. Using this technique, the soft cores are produced by directly compacting a blend of the active agent and any other appropriate inactive ingredients, i.e., excipients (e.g. flavoring, binders, lubricants, etc.). Any conventional compacting methods for forming a chewable dosage form may be used to make the soft core of the present invention. These methods include, but are not limited to, dry granulation followed by compression, and wet granulation followed by drying and compression. Compression methods include rotary compression, compacting roller technology, such as a chilsonator or drop roller, or by molding, casting, or extrusion technologies. These methods are well known in the art, and are described in detail in, for example, Lachman, et al., *The Theory and Practice of Industrial Pharmacy*, Chapter 11, (3$^{rd}$ Ed. 1986).

Conventional excipients useful in the present invention for direct compression include fillers, such as water soluble compressible carbohydrates, e.g., sucrose, mannitol, sorbitol, maltitol, xylitol, lactose, and mixtures thereof; binders, such as cellulose, cellulosic derivatives, polyvinyl pyrrolidone, starch, modified starch, and mixtures thereof, disintegrants, such as sodium starch glycolate, crosspovidone, crosscarmellose, microcrystalline cellulose, starch, and the like, lubricants, such as magnesium stearate, stearic acid, talc, and waxes; glidants, such as colloidal silicon dioxide, sweeteners, including aspartame, acesulfame potassium, sucralose and saccharin; flavors, acidulants, antioxidants, preservatives, surfactants, wetting agents, and coloring agents.

The soft core of the present invention may be shaped, in other words, formed, by a variety of methods known in the art. One such method utilizes placing a pre-determined volume of particles or components into a die cavity of a rotary tablet press, which continuously rotates as part of a die table from the filling position to a compaction position. At the compaction position, the particles are compacted between an upper punch and a lower punch. The die table then rotates to an ejection position, at which the resulting tablet is pushed from the die cavity by the lower punch and guided to an ejection chute by a stationary take-off bar.

One form of the soft core of the present invention may be a tablet. Tableting is typically carried out such that the tablet is relatively soft. The hardness of the tablet is up to about 15 kiloponds per square centimeter (kp/cm$^2$), e.g., about 1 to 8 kp/cm$^2$ or about 2 to 6 kp/cm$^2$. As used herein, the term hardness is used to describe the diametral breaking strength as measured by conventional pharmaceutical hardness testing equipment, such as a Schleuniger Hardness Tester. In order to compare values across different size tablets, the breaking strength is normalized for the area of the break (which may be approximated as tablet diameter times thickness). This normalized value, expressed in kp/cm$^2$, is sometimes referred in the art as tablet tensile strength. A general discussion of tablet hardness testing is found in Leiberman et al., *Pharmaceutical Dosage Forms—Tablets*, Volume 2, 2$^{nd}$ ed., Marcel Dekker Inc., 1990, pp. 213-217, 327-329.

Optionally, the dosage form of the present invention, either with or without active agent, can be molded, deposited or extruded under methods commonly known in the art.

For example, the dosage form shape of the present invention may be formed by the depositing technique known to those in the art. This process involves the filling (generally by gravity) of a fluid (e.g., liquid, suspension, melt, etc.) into a mold. Generally, the mold is open at the top so that the finished form has one flat, or un-shaped, surface. The mold is typically a starch mold that is formed by filling a tray with starch, leveling the surface of the starch, then imprinting the surface of the starch with impressions from a mold board. The impressions can be any of a variety of shapes and sizes, however vertical sides are not desirable. The molding starch is generally dry (usually less than 6% moisture). It is possible to use sugar in place of starch in this process, or to use brittle molds of plastic, metal, or other materials which are first sprayed with a release agent. See, for example, *Sugar Confectionery Manufacture*, Van Nostrand Reinhold, 1990, pp. 205-206.

The optional extruding technique involves feeding a maleable semi-solid starting material into an extruder. The extruder applies pressure to force the mass through an orifice that shapes the dosage form in two dimensions, generally into a rope, which is cut to form pieces. The starting material can be either hot or cold.

Optionally, three-dimensional molded shapes can be formed from a semi-solid starting material using a uniplast mold, chain mold, or calendar roll. Three-dimensional molded shapes can be formed from a liquid or molten starting material by injection molding.

Conventional excipients useful in the present invention for molded, deposited, or extruded forms include fillers, such as water soluble simple and complex carbohydrates, e.g., sucrose, glucose, fructose, maltose, lactose, maltodextrins, low and high D.E. corn syrups, and high fructose corn syrups. Polyhedric alcohols and hydrogenated starch hydrolysates e.g., mannitol, sorbitol, maltitol, erythritol, andxylitol. Hydrocolloids e.g., natural and modified gums, cellulosics, modified cellulosics, pectins, mucillages, starch and modified starches, noncellulosic polysaccharides, algal polysaccharides and mixtures thereof. More specifically the hydrocolloids include starch, gelatin, soy protein and soy protein isolates, egg albumin, agar-agar, microcrystalline cellulose, methylcellulose, hydroxypropyl cellulose (HPC), hydroxypropyl methylcellulose (HPMC), xanthan gum, carrageenan gum, locust bean gum, alginates, acacia, carboxymethylcellulose (CMC), karaya gum, acacia gum, sodium alginate, sodium CMC, guar gum, tragacanth, mixtures of the hydrocolloids and the like. Other suitable water-soluble polymers include inulin, fucoidan, polymerized maltotriose and the like. Artificial sweeteners known in the art e.g., saccharin, aspartame, sucralose, and acesulfame-potassium, as well as flavors, edible glazes and waxes, acidulants, antioxidants, preservatives, surfactants, wetting agents, and coloring agents.

The brittle coating may be applied to the soft core in any manner, such as spraying, roller coating, dipping, panning, or enrobing, which are known in the art. The brittle coating may include components, such as natural or artificial sweeteners, colorants, flavors, plasticizers. The brittle shell of the present invention is present in a weight ratio of active agent particles to shell that is from about 1.0:0.5 to about 1.0:15, e.g., about 1.0:2 to about 1.0:12, or from about 1.0:4 to about 1.0:9.

Generally, panning involves applying a liquid coating to a pellet, which is then solidified, usually by drying the coating. The brittle-shell coating layer is built up by successive coating and drying steps.

The brittle shell of the present invention may include carbohydrates, such as mannitol, sorbitol, maltitol, xylitol, dextrose, dextrose monohydrate, maltodextrin, fructose, sucrose, lactose, maltose, xylose, sucralose, and mixtures thereof.

Conventional panning procedures generally coat with sucrose, but recent advances in panning have allowed the use of other carbohydrate materials to be used in the place of sucrose. Some of these include, but are not limited to, dextrose, maltose, xylitol, isomalt, hydrogenated isomaltulose and other new polyols or a combination thereof. These materials may be blended with panning modifiers including, but not limited to, gum arabic, maltodextrins, corn syrup, gelatin, cellulose-type materials like carboxymethyl cellulose or hydroxymethyl cellulose, starch and modified starches, vegetable gums like alginates, locust bean gum, guar and gum tragacanth, insoluble carbonates like calcium carbonate or magnesium carbonate, and talc. Antitack agents may also be added as panning modifiers, which allow the use of a variety of carbohydrates and sugar alcohols to be used in the development of new panned or coated gum products.

Bulk sweeteners used in panning are very stable and highly water soluble, and can be easily added to a sugar solution prepared for sugar panning. Polydextrose may be added in a liquid form to the sucrose coating or any other sugar or alditol coating. Polydextrose can also be added as a powder blended with other powders often used in some types of conventional panning procedures. Polydextrose may be added to the liquid syrup and used as a panning modifier with other sugar and sugar alcohol syrups, such as dextrose, sucrose, xylitol and palatinit. Polydextrose may act as a binder to, and film former for, the sugar or sugar alcohol coating.

It is known to improve coating processes using sugars or alditols to add a powder coating after a liquid coating. The powder coating may include polydextrose, maltodextrin, gelatin, cellulose derivatives, starches, modified starches, vegetable gums, fillers, e.g., talc and calcium carbonate dextrose, sucrose, xylitol. This is believed reduce stickiness and allow a faster build-up of coating.

The thickness of the coatings is typically any thickness from about 500 μm to about 3000 μm. The weight percentage of the exterior coatings may range from, based upon the total weight of delivery system, active agent, and exterior coating, from about 10% to about 60%, e.g. from about 20% to about 50%, and about 30% to about 45%.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLES

Example 1

Preparation of Compressed Cores

A color blend was prepared by combining 563.5 g. Crospovidone NF, 28.17 g. Aspartame NF, 42.26 g. citric acid anhydrous powder USP, and 7.04 g. FD&C Yellow #6 A1 Lake in a polyethylene bag. After the bag was sealed, the combination was mixed by inverting the bag 20 times. The resulting color blend was screened through a 40 mesh hand screen, and stored in a plastic bag.

Separately, 352.2 g of Hydrogenated Vegetable Oil (Wecobee S) was heated in an oven to 56° C.

In a 5 gallon Hobart mixer, 4095.0 g coated acetaminophen granulation (containing 86 wt % active) and 28.17 g Aspartame NF were combined and mixed at speed setting 1 for 2 minutes. The resulting blend was heated in an oven to 54° C.

176.1 g of the heated hydrogenated vegetable oil was added to the heated ingredients in the Hobart bowl, while mixing for 2 minutes. Mixing was then continued for an additional 2 minutes. The ingredients in the bowl were then allowed to cool to 29° C., about 46 minutes.

640.97 g of the color blend, 1655.2 g Sorbitol NF (Sorbidex P 16616), 1655.2 g Dextrose monohydrate USP (Cerelose), and 42.26 g N&A Orange flavor were to the cooled mixture in the Hobart bowl, and mixed at speed setting 1 for 3 minutes:

After mixing, 49.30 g Magnesium Stearate NF and 457.8 g Xylitol NF (Xylisorb 90) were added and the resulting composition was mixed at speed setting 1 for 2 minutes. The resulting granulation was discharged into a plastic bag. Final granulation weight was 8774 g.

The granulation was then compressed on a Manesty Beta-press using 19/32" round, deep concave tooling to the following physical specification targets:
Weight: 1249.4 mg
Brittleness: 1.5 kp
Thickness: 0.350"
Friability (5 tablets): none break prior to 10 drops.

Example 2

Pan Coating of Compressed Cores

TABLE I

| Ingredients | Unit Wt (mg) | Batch Wt (g) |
| --- | --- | --- |
| PART 1 (1550 Units) Tablet Core from example 1 | 624.7 | 1935.7 |
| Hydrogenated Vegetable Oil (Wecobee M) | 55.0 | 341.0** |
| PART 2 (1550 Units) Tablet Core from example 1 (Post HVO) | 1304.4 | 2021.8 |
| Gum Arabic (Coatingum L)(Also used in Part 5) | 15. | 93.0** |
| Purified Water USP* (Also used in Part 5) | 45. | 279.0** |
| Sucrose NF (Bakers Special) | 150. | 465 |
| Citric Acid Anhydrous USP Powder | 2.0 | 3.10 |
| Firmenich N&A Orange 57.842/AP 05.51 | 1.0 | 1.55 |
| PART 3 (1550 Units) | 1472.4 | 2250.3 |
| Tylenol Melt-Tab Core (Post Soft Pan) | | |
| Sucrose NF (Extra Fine Granular)(Also used in Part 6) | 200. | 1240.0** |
| Purified Water USP* (Also used in Part 6) | 100. | 620.0** |
| Opalux Orange AS-2343 (Also used in Part 6) | 0.6 | 3.72** |
| PART 4 (1550 Units) Tablet Core from example 1 (Post Brittle Pan) | 1673.0 | 2525.0 |
| Carnuba Wax NF | 0.9 | 1.40 |
| TOTAL | 1673.9 | |

*Removed during processing;
**Includes 100% excess of theoretical amount;
***See calculation in Batch Record Label Claim: 500 mg Acetaminophen/tablet 1550 units of tablet cores from Example 1 were transferred into a plastic bag, and refrigerated 16° C. 341.0 g of hydrogenated vegetable oil (Wecobee M) was heated and maintained at a temperature of about 48 to about 52° C. in a pan on a stovetop. The refrigerated tablet cores were transferred into a 16" conventional coating pan (Keith Machinery Corp., Lindenhurst, N.Y.) with four #14 tubing baffles. The cooling end of a vortex tube was mounted in the pan's opening. The tablet cores were tumbled at a pan speed setting between 20 to 35. A portion of the heated hydrogenated vegetable oil (Wecobee M) was added by ladling onto the rotating cores until a weight gain of 50 to 60 mg per tablet was obtained. The cores were cooled using the Vortex Tube and stored at 10 to 20° C. in a refrigerator.

Soft panning of the cores was carried out using a 25 wt % gum arabic solution that was prepared by adding 93.0 g of gum arabic (Coatingum L) to 279.0 g of Purified Water in a stainless steel container while mixing, and continuing to mix for 1 hour. The solution was then deaerated under vacuum for about 6 hrs.

The 1550 units of refrigerated tablet cores from were transferred into the 16" conventional coating pan with no baffles. The tablet cores were then tumbled at a pan speed between 20 to 40. The rotating cores were wetted with 20.2 g of the 25% Gum Arabic Solution. 141.3 g of sucrose NF (Bakers Special) was added, and tumbling was continued for 30 minutes at a pan speed setting of 30 until cores appeared dry.

The rotating cores were wetted using an additional 40.0 g of the 25% gum arabic solution. The following ingredients were then added: 135.4 g sucrose NF (Bakers Special); 3.10 g citric acid anhydrous USP powder; 1.55 g Firmenich N&A orange 57.842/AP 05.51; and tumbling was continued for 30 minutes at a pan speed setting of 25 until cores appeared dry.

An additional 12.0 g of the 25% Gum Arabic Solution was added to wet the rotating cores. 35.6 g of sucrose NF (Bakers Special) was added, and tumbling was continued for 25 minutes at a pan speed setting of 25 until cores appeared dry. The resulting tablets were removed from the pan and spread onto trays and stored for 16 hours at ambient conditions (approximately 72° F./50% RH). Amount of gum arabic solution used: 72.2 g. Amount of Sucrose used: 312.3 g. Weight gain of tablets after coating: 203 mg/tablet A 67% sucrose solution was prepared by adding 620.0 g of purified water into a stainless steel container, containing a magnetic stir bar. While mixing to create a vortex, 1240.0 g of sucrose NF (Extra Fine Granular) was added. The container was then covered with aluminum foil and heated to 60-65° C. while continuing to mix. The temperature was maintained at 60-65° C. with mixing for 20 minutes. The solution was then allowed to cool to 37-43° C., and temperature then maintained in this range.

594.0 g of the 67% sucrose solution was added into a stainless steel container, containing a magnetic stir bar. While mixing to create a vortex, 3.72 g of orange lake dye (OPALUX AS-2343 available from Colorcon, West Point, Pa.) was added, then the resulting orange lake dye/sucrose solution was covered with aluminum foil and heated to 40° C. and mixed for an additional 5 minutes.

Brittle Panning of the dosage form was carried out using 1550 units of the tray dried soft panned cores. The cores were placed into a 16" conventional coating pan with no baffles and with a room temperature air blower in the pan's opening. Pan speed was set to about 20, in order to maintain adequate tumbling. Fourteen applications of the previously prepared 67% Sucrose Solution were applied onto the rotating cores by hand ladling. Eight applications of orange lake dye sucrose solution were applied onto the rotating cores by hand ladling. Tablets were removed from the pan and spread onto trays and stored for 22.5 hours at ambient conditions (approximately 72° F./50% RH). Amount of 67% SUCROSE SOLUTION used: 288.9 g. Amount of lake orange sucrose solution used: 130.2 g. Weight gain of tablets after coating: 177.2 mg/tablet.

Polishing 1550 units of the tray dried tablet cores was carried out by transferring the tablet cores into the 16" conventional coating pan set up with four #14 tubing baffles. The tablets were tumbled at a pan speed setting between 20 and 40, in order to maintain adequate tumbling. 1.40 g of carnuba wax was added to the rotating cores. Tumbling was continued for 30 minutes. The polished finished product was stored in a plastic bag at room temperature. Weight gain of tablets after polishing was 1627.4 mg/tablet Example 3

Pectin Core

TABLE II

| Ingredients | Unit Wt (mg) | Batch Wt (g) |
| --- | --- | --- |
| CITRIC ACID SOLUTION 50% (w/v) | N/A | 500.0* |
| Purified Water USP | | |
| Citric Acid USP, Anhydrous Powder | N/A | 250.0* |
| TOTAL | | 750.0 |

TABLE III

| Ingredients | Unit Wt (mg) | Batch Wt (mg) |
| --- | --- | --- |
| BOB SYRUP | 135.8*** | 148.00** |
| Purified Water USP † | | |
| Sodium Citrate, Anhydrous Powder | 3.6 | 2.00 |
| Citric Acid USP, Anhydrous Powder | 3.3 | 1.85 |
| Pectin (Grinsted XSS 100) | 13.4 | 7.50 |
| Sucrose NF (Extra Fine granular) | 44.8 | 25.00 |
| [Pectin Dissolution] | | |
| Sucrose NF (Extra Fine granular) | 415.6 | 232.10 |
| Corn Syrup 42/43 | 268.6 | 150.00 |
| Coated Acetaminophen Gran. (76.5 % APAP) | 104.6 | 58.41 |
| N&A Tutti Frutti flavor | 3.6 | 2.00 |
| Citric Acid Solution 50% w/v | 6.6 | 3.70 |
| TOTAL | 999.9*** | 558.41*** |

*Stock Solution made in excess
**Weight prior to cook step
***Weight after cook step
†Theoretical Batch Weight of Purified Water USP after the cook step is 75.85 g. Label Claim: 80 mg Acetaminophen/unit A citric acid solution (50% w/v) was made by placing 250 g. of citric acid USP, anhydrous powder in a 500 mL volumetric flask. Purified water was added to the 500 mL volumetric flask until approximately ¾ filled. The flask was placed into a sonic bath and sonicated for two hours. The flask was then removed from the sonic bath and allowed to cool to 20° C. (19° C.-21° C.). When the solution temperature reached 20° C., purified water was added to the 500 ML mark. The solution was mixed by inverting the stoppered flask several times.

Separately, a 600 mL glass beaker containing 148.00 g. of purified water was heated to 70° C. (69° C.-72° C.) on a heated stir plate. The water was then mixed using a mixer equipped with a 1.5 in. diameter, 3-blade propeller. The sodium citrate, anhydrous powder and citric acid USP, anhydrous powder were to the hot purified water while mixing. Mixing was continued until the solution was clear (about 3 minutes).

7.50 g. of pectin (Grindsted XSS 100) and 25.00 g. of sucrose NF (extra fine granular) [pectin dissolution] were added to a small plastic bag and blended by inverting the bag several times. The pectin/sucrose blend was then added to the hot buffer solution formed above and mixing was continued to produce a pectin buffer dispersion.

Bob syrup was made by placing 150.0 g. corn syrup was into a tared pan. 232.1 g. of sucrose NF (extra fine granular) were added to the pan. While mixing with the spatula, the ingredients were heated to a temperature of 102° C. (100° C.-105° C.). The pectin buffer dispersion prepared was added to the pan with continued heating of the ingredients. Heating was continued, evaporating water, until the weight of the ingredients was between about 492 g to about 496 g., with the target being 494.3 g.

The following ingredients were added to the bob syrup in the order listed, while mixing with a spatula: 2.00 g. N&A Tutti Frutti flavor; 59.26 g. coated acetaminophen particles (C-873-1); and 3.70 g. citric acid solution 50% (w/v).

The batch was then transferred to a 32 oz. heated pressure pot, which had been equilibrated to 80° C. (75° C.-85° C.). The top was placed on the heated pressure pot and sufficient air pressure was applied to allow product to flow from the depositing nozzle into a 5 cc syringe. About 1 g. (0.7 g.-1.1 g.) samples were deposited into a 50/50 mixture of MELOJEL brand corn (National Starch and Chemical Co., Bridgewater, N.J.) food grade starch from dent & NU MOULD brand (National Starch and Chemical Co. Bridgewater, N.J.) food grade corn starch with mineral oil imprinted with a jelly bean shape, using 5 cc plastic syringes.

The starch molds were placed into a forced air oven at 49° C. (47° C.-51° C.) for about 22 hours. The pectin cores were removed from the mold starch and stored at room temperature in a plastic bag. Average weight of 50 cores was about 765 mg/core.

Example 4

Coating of Pectin-based Cores

Cores from Example 3 were placed onto a 10 mesh screen. Excess molding starch was removed by passing compressed air over the cores while gently agitating the screen. Average weight of 50 cores: 728.4 mg/core.

A 25% Gum Arabic Solution was prepared by adding 38.4 g of gum arabic to 115.1 g of purified water in a stainless steel container and mixing for 1 hour. The solution was allowed to stand at ambient conditions for about 16 hours to deaerate.

1400 units of the above cores were transferred to a 16" conventional coating pan with four #14 tubing baffles. The cores were tumbled at a pan speed setting of 60, while adding 6.72 g of the 25% gum arabic solution from above to wet the rotating cores. 91.0 g of sucrose NF (Bakers Special) was added and tumbling continued for 25 minutes until the cores appeared dry. The rotating cores were again wetted by ladeling an additional 11.21 g of the 25% gum arabic solution. 84.1 g of sucrose NF (Bakers Special) was added. Tumbling was continued for another 15 minutes until cores appeared dry. The rotating cores were again wetted by ladeling an additional 10.17 g of the 25% gum arabic solution. 74.0 g of sucrose NF (Bakers Special) was then added. Tumbling was continued for 10 minutes until cores appeared dry. The rotating cores were again wetted by ladeling 9.90 g of the 25% gum arabic solution. 55.0 g of sucrose NF (Bakers Special) was added, and tumbling continued for 18 minutes until the cores appeared dry. The cores were then removed from the pan, spread onto trays and stored for about 22.5 hours at ambient conditions (approximately 72° F./50% RH). Weight gain of cores after soft panning was about 195.8 mg/core.

A Sucrose/Lake red dye (Opalux Red AS-1662-D, available from Colorcon, West Point, Pa.) solution was prepared by mixing 966.3 g of sucrose NF into 414.7 g of purified water in a stainless steel container using a magnetic stir bar. The container was covered with aluminum foil and heated to about 60—about 65° C. with continued mixing. The solution was mixed for an additional 20 minutes at about 60—about 65° C. at which time the solution was visually clear. 9.2 g of lake red dye was added to the sucrose NF solution, the foil replaced, and mixing continued for 10 minutes while maintaining temperature between about 60—about 65° C.

1400 units of cores were transferred into a 16" conventional coating pan with four #14 tubing baffles, with a room temperature air blower mounted in the pan's opening. The cores were tumbled at a pan speed setting of 40, while applying 20 applications of sucrose/lake red dye in 10 to 18 g. increments with 3 to 8 minutes drying time in between applications.

The pan speed was reduced to a setting of 25, and an additional 10 applications of Sucrose/Lake Red Dye Solution were applied in increments of 8 to 13 g. with 6 to 12 minutes drying time in between applications. The cores were removed from the pan, spread onto trays, and stored for 21 hours at ambient conditions. Weight gain from brittle panning was about 217.2 mg/core.

1400 units of cores from step F were transferred into a 16" conventional coating pan with four #14 tubing baffles. The cores were tumbled at a pan speed setting of 35. About 1.17 g of carnuba wax was added to the rotating cores, and tumbling continued for 10 minutes. Weight gain after polishing was about 7.6 mg/unit.

What is claimed is:

1. A texture masking oral dosage form comprising:
   (a) a unitary molded soft core comprising a plurality of active agent particles having an average size of from about 150 μm to about 500 μm, a hydrocolloid, and water; wherein the active agent particles have a gritty texture and
   (b) a soft panned brittle shell encasing the soft core in an amount of from about 20% to about 50% of the total weight of the texture masking oral dosage form and a thickness of from about 500 μm to about 3000 μm, wherein the weight ratio of active agent particles to shell is from about 1.0:0.5 to about 1.0:15 in the texture masking oral dosage form and wherein the soft core is pectin or gelatin based.

2. An oral dosage form of claim 1, wherein the weight ratio of active agent particles to shell is from about 1.0:2 to about 1.0:12.

3. An oral dosage form of claim 2, wherein the weight ratio of particles to shell is from about 1.0:4 to about 1.0:9.

4. An oral dosage form of claim 1, wherein the active agent is selected from the group consisting of acetaminophen, ibuprofen, pseudoephedrine, dextromethorphan, diphenhydramine, chlorpheniramine, calcium carbonate, magnesium hydroxide, magnesium carbonate, magnesium oxide, aluminum hydroxide, mixtures thereof, and pharmaceutically acceptable salts thereof.

5. An oral dosage form of claim 4, wherein the active agent is acetaminophen or ibuprofen.

6. An oral dosage form of claim 5, wherein the active agent is acetaminophen.

7. An oral dosage form of claim 5, wherein the active agent is ibuprofen.

8. An oral dosage form of claim 3, wherein the active agent is selected from the group consisting of acetaminophen, ibuprofen, pseudoephedrine, dextromethorphan, diphenhydramine, chlorpheniramine, calcium carbonate, magnesium hydroxide, magnesium carbonate, magnesium oxide, aluminum hydroxide, mixtures thereof, and pharmaceutically acceptable salts thereof.

9. An oral dosage form of claim 8, wherein the active agent is acetaminophen or ibuprofen.

10. An oral dosage form of claim 9, wherein the active agent is acetaminophen.

11. An oral dosage form of claim 9, wherein the active agent is ibuprofen.

12. A texture masking oral dosage form comprising:
(a) a unitary molded soft core comprising a plurality of acetaminophen particles having an average size of from about 150 μm to about 500 μm, a hydrocolloid, and water; wherein the acetaminophen particles have a gritty texture and
(b) a soft panned brittle shell enveloping the soft core in an amount of from about 20% to about 50% of the total weight of the texture masking oral dosage form and a thickness of from about 500 μm to about 3000 μm, wherein the weight ratio of active agent to shell is from about 1.0:4 to about 1.0:9 in the texture masking oral dosage form and wherein the soft core is pectin or gelatin based.

13. A texture masking oral dosage form comprising:
(a) a unitary molded soft core comprising a plurality of ibuprofen particles having an average size of from about 150 μm to about 500 μm, a hydrocolloid, and water; wherein the ibuprofen particles have a gritty texture and
(b) a soft panned brittle shell enveloping the soft core in an amount of from about 20% to about 50% of the total weight of the texture masking oral dosage form and a thickness of from about 500 μm an to about 3000 μm, wherein the weight ratio of particles to shell is from about 1.0:4 to about 1.0:9 in the texture masking oral dosage form and wherein the soft core is pectin or gelatin based.

14. The dosage form of claim 1, wherein the unitary molded soft core is formed in a starch mold, a sugar mold, or a brittle mold.

* * * * *